United States Patent [19]

Vaughan

[11] 4,320,015
[45] Mar. 16, 1982

[54] MAGNESIUM SALTS OF N-CARBOXYAMINO ACID

[75] Inventor: Ronald J. Vaughan, Orinda, Calif.

[73] Assignee: Chevron Research Company, San Francisco, Calif.

[21] Appl. No.: 53,448

[22] Filed: Jun. 29, 1979

[51] Int. Cl.³ .............................................. C10M 1/54
[52] U.S. Cl. ................................... 252/33.6; 562/555; 426/321; 252/527; 252/546
[58] Field of Search ....................... 252/33.6; 562/555

[56] References Cited

U.S. PATENT DOCUMENTS

| | | | |
|---|---|---|---|
| 3,524,814 | 8/1970 | Sabol et al. | 252/33.2 |
| 3,857,790 | 12/1974 | Saunders et al. | 252/40.7 |
| 4,034,037 | 7/1977 | Jordan | 562/433 |
| 4,059,536 | 11/1977 | Lallement et al. | 252/33.3 |

*Primary Examiner*—Winston A. Douglas
*Assistant Examiner*—Y. Harris-Smith
*Attorney, Agent, or Firm*—D. A. Newell; J. J. DeYoung

[57] ABSTRACT

Disclosed are the magnesium salts of N-carboxyamino acids, a process for their preparation, and their use of lubricating oil additives.

6 Claims, No Drawings

MAGNESIUM SALTS OF N-CARBOXYAMINO ACID

FIELD OF THE INVENTION

This invention relates to a method for preparing the magnesium salts of N-carboxyamino acids, lubricating oil additives containing said salts, particularly overbased lubricating oil additives, to the additives themselves, and to lubricating oil compositions containing the additives.

With the increasing severity of operating conditions of the engines caused in part by the deteriorating quality of fuels for these engines, there is a need for compositions which can lubricate and maintain the cleanliness of the engine while, at the same time, neutralizing large quantities of acids which result from the use of fuels having an increased sulfur content. Conventional lubricating oil additives used to neutralize base contain ash-forming components, generally metallic salts. As increasing amounts of the acid-neutralizing components are used in formulations, the amount of ash in the composition often exceeds the amount of ash for which the engine is designed.

New additives are needed which can maintain the cleanliness of the engine and neutralize the large amounts of acid being formed from the increased use of a high-sulfur fuel, while at the same time not exceeding the ash requirements of the engines being lubricated.

The preparation of conventional additives which are overbased to obtain additional acid-neutralizing efficiency is taught in U.S. Pat. No. 3,126,340. The additive described in this patent is prepared by treating a lubricating oil sulfonate dispersant with an alkaline earth metal oxide and hydroxide and then introducing carbon dioxide and ammonia into the mixture followed by heating the mixture in the presence of water to convert and ammonia to an alkaline earth metal carbonate. The alkaline earth metal carbonate is the acid-neutralizing portion of the composition.

U.S. Pat. No. 3,524,814 teaches the preparation of an overbased alkaline earth metal sulfonate by introducing a mixture of carbon dioxide and ammonia, in an amount sufficient to form a catalytic amount of ammonium carbamate, into a lubricating oil having in suspension a neutral alkaline earth metal sulfonate containing an alkaline earth oxide. After the catalytic amount of ammonium carbamate is preformed, carbon dioxide is continuously introduced into the reaction mixture until substantially all of the alkaline earth oxide is converted to alkaline earth metal carbonate. The metallic carbonate provides the reserve alkalinity in the sulfonate. As a posttreatment step, water is added to the reaction mixture. The addition of water decomposes any ammonium carbamate still present in the reaction mixture.

U.S. Pat. No. 4,034,037 teaches the production of metal carboxylates or N-organic substituted carbamates by reaction of a carboxylic acid or carbon dioxide with an amine in the presence of a soluble metal salt. These salts are disclosed to be useful as lubricating oil additives.

The production of some alkali and alkaline earth metal salts of N-carboxyamino acids in aqueous and alcohol systems is known in the art. See, for example, the various articles by M. Siegfried, Z. Physiol. Chem. 44,85, (1905), which disclose the production of barium and calcium salts of N-carboxyamino acids. The mercury salts of N-carboxyamino acids are disclosed in C. Neuberg and J. Kerb, Biochemische Z. 40,498 (1912). The sodium salt of N-carboxyglycine is disclosed in A. C. Farthing, J. Chem. Soc. 1950, 3213.

SUMMARY OF THE INVENTION

Claimed are the magnesium salts of N-carboxyamino acids.

DETAILED DESCRIPTION OF THE INVENTION

It has been surprisingly found that the magnesium salts of N-carboxyamino acids of the present invention are stable in the presence of water at elevated temperatures. This is particularly surprising and unexpected in view of the fact that the calcium, barium, strontium, and sodium, amino acid carbamates are not stable in water. This property is particularly useful since water at elevated temperatures comes in contact with lubricating oils in the operation of an internal combustion engine. The magnesium salts of N-carboxyamino acids of the present invention have many uses, particularly as lubricating oil additives, chelating agents, as food preservatives and as extenders for household detergents, etc.

The compound of the present invention may be formed from the reaction of carbon dioxide with a basically reacting magnesium compound and an amino acid of the structural formula I, below. The preferred products are the magnesium salts of N-carboxyamino acid represented by structural formula II, below.

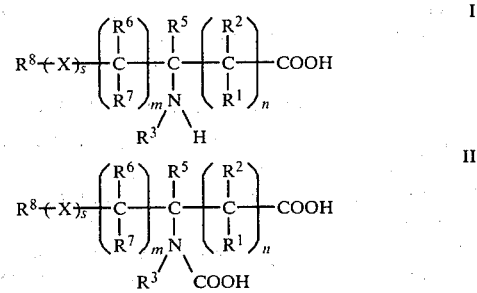

wherein:
$R^1$, $R^2$, $R^5$, $R^6$ and $R^7$ are independently:
  hydrogen,
  an alkyl of 1 to 20 carbons,
  a carboxy alkyl group of 2 to 20 carbons,
  a hydroxyalkyl group of 1 to 20 carbons,
  an aryl of 6 to 10 carbons,
  an amino alkyl group of 1 to 20 carbons, having hydrogen or alkyl of 1 to 6 on the nitrogen atom, or
  an amino carboxy alkyl group of 2 to 20 carbons,
$R^1$ and $R^2$ may be connected directly or through an atom of O, S or N, to form a 5 or 6 membered ring;
$R^3$ is:
  hydrogen,
  an alkyl of 1 to 20 carbons,
  an aryl of 6 to 12 carbons,
  an alkaryl of 7 to 20 carbons,
  an aralkyl of 7 to 20 carbons,
  a carboxyalkyl of 2 to 20 carbons,
  a hydroxyalkyl of 2 to 20 carbons,
  an amino alkyl of 2 to 20 carbons,
  a polyaminoalkyl of 4 to 20 carbons and 2 to 10 amino groups;
n is 0 to 6,
M is 0 to 6, s is 0 or 1;

$R^3$ and $R^5$ may be joined to form a 5 or 6 membered heterocyclic ring having from 0 to 1 additional heteroatoms selected from the group of O, S, NR wherein R is an alkyl group of 1 to 6 carbons.

$R^5$ and $R^6$ may be joined directly or through an atom of O, S or N to form a 5 or 6 membered ring.

X is a connecting diradical chosen from the group, —O—, —S—, —SS—, $-(CH_2)_p$, where p is 1 to 6, and

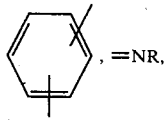, =NR, $R^8$ is:
- hydrogen,
- an alkyl of 1 to 20 carbons,
- a hydroxyalkyl of 1 to 20 carbons,
- an aryl of 6 to 12 carbons,
- an alkaryl of 7 to 20 carbons,
- an aralkyl of 7 to 20 carbons,
- an aminoalkyl of 1 to 20 carbons,
- a carboxyalkyl of 2 to 20 carbons,
- a carboxy group,
- an amino group having 0, 1 or 2 substituents as defined for $R^3$, and
- where s is not phenyl, $R^8$ may have the same structure as is attached to the opposite end of the —X— connecting group.

METHODS OF PREPARATION

The magnesium N-carboxyamino acid salts of the present invention are preferably prepared by reacting the corresponding amino acid with a basically reacting magnesium containing compound and carbon dioxide in the presence of a suspending agent for said basically reacting magnesium compound and in the presence of a reaction promoting amount of a hydroxylic promoter. The N-carboxyamino acid salts can also be prepared by the reaction of the basically-reacting magnesium compound, the amino acid, and carbon dioxide in water or mixtures of water and another hydroxylic solvent. The preparation of alkaline earth metal salts of amino acid, including the magnesium salts, is also described in my copending application Ser. No. 973,871, filed Dec. 28, 1978, now U.S. Pat. No. 4,218,328 the entire disclosure of which is incorporated herein by reference.

The Amino Acid

By "amino acid" is meant any organic acid containing at least one basic amino (—NH) group and at least one acidic carboxyl (—COOH) group. Mixtures of different amino acids can be used.

Representative amino acids useful in preparing the salts of the present invention include: glycine, alanine, Betaalanine, valine, leucine, isoleucine, phenylalanine, serine, threonine, tyrosine, methionine, 6-aminohexanoic acid, proline, hydroxyproline, tryptophan, histidine, lysine, hydroxylysine, arginine, aspartic acid, asparagine, glutamic acid, glutamine, cysteine and cystine, aminoethylcysteine and iminodiacetic acid.

Particularly preferred are the amino acids which are readily available in commercial quantities such as glycine Also particularly preferred are the alpha-amino acids.

Numerous processes for the production of amino acids are well known in the art and the amino acids of the present invention can be prepared in situ, if desired. For example, glycine can be prepared from the well-known reaction of ammonia, formaldehyde and sodium cyanide, as taught, for example, in U.S. Pat. No. 2,663,713, the disclosure of which is incorporated herein by reference.

The nitrogen portion of the amino acid serves as a source of supply of non-ash-forming basic material in the lubricating oil additives of this invention.

THE BASICALLY REACTING MAGNESIUM COMPOUND

The basically reacting magnesium compound is any magnesium compound which reacts under basic conditions, i.e., at a pH greater than 7.0, to form a salt of an organic acid. Typical of such magnesium compounds are magnesium oxide, hydroxide or methoxide. Useful alkoxides are the lower-molecular-weight alkoxides such as methoxide, ethoxide, t-butoxide, and the like. Preferred are magnesium oxide or magnesium hydroxide.

THE SUSPENDING AGENT

When it is desired to form the magnesium N-carboxyamino acid salt suspended in a hydrocarbon medium, a suspending agent is used. The suspending agent, which must be oil-soluble, is used to keep the basically reacting magnesium component in solution so that it can be an effective portion of the additive composition. Many of the useful suspending agents also have dispersant activity in the final lubricating oil additive composition. Typical suspending agents include alkali metal or alkaline earth metal hydrocarbylsulfonates, hydrocarbyl succinimides, hydrocarbyl succinates, hydrocarbyl succinic anhydrides, alkali metal or alkaline earth metal alkylphenates, alkylphenol-type Mannich bases and alkaline earth metal salts of such Mannich bases. Mixtures of suspending agents are also useful in carrying out the process of this invention.

The alkali metal and alkaline earth metal hydrocarbyl sulfonates useful in the process of this invention are well known in the art. The hydrocarbyl group must have a sufficient number of carbon atoms to render the sulfonate molecule oil soluble. Ordinarily, the hydrocarbyl portion has at least 20 carbon atoms and may be aromatic or aliphatic, but is usually alkylaromatic. Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

Succinimide dispersants are also well known in the art, and a general method for their preparation is found in U.S. Pat. Nos. 3,219,666, 3,172,892 and 3,272,746, the disclosures of which are hereby incorporated by reference. These compositions are prepared by reacting an oil-soluble alkyl or alkenyl succinic acid or anhydride with a nitrogen-containing compound. The succinimide may be of the type commonly known as a mono- or bis-succinimide. Preferred nitrogen compounds used in making the succinimides are those known as the ethyleneamines, and particularly preferred are triethylenetetraamine and tetraethylenepentamine. The preferred alkyl or alkenyl groups contain from 50 to 300 carbon atoms, and the most preferred compositions are prepared from polyisobutylene. When this type of suspending agent is employed, the amine portion will contribute to the alkalinity value.

The oil-soluble alkyl or alkenyl succinic anhydrides used in preparing the succinimides are themselves useful as suspending agents; however, they are most preferred for use as co-suspending agents, particularly in combination with a sulfonate suspending agent. Preferably the alkyl or alkenyl portion contains from 50 to 300 carbon atoms.

The succinate esters are prepared by reacting an alcohol with an alkenyl or alkyl succinic anhydride as described above, using a procedure such as that described in U.S. Pat. Nos. 3,381,022 and 3,522,179, the disclosures of which are hereby incorporated by reference. Ordinarily the alkyl or alkenyl group contains from 50 to 300 carbon atoms.

Alkali metal and alkaline earth metal phenates are well known in the art and are the alkali metal or alkaline earth metal salt of an oil-soluble alkyl-substituted phenol. The composition may be sulfurized. Typical phenates are prepared by neutralizing a $C_{8-28}$ alkylphenol with calcium hydroxide or oxide.

Mannich bases are useful suspending agents. Mannich bases are prepared by reacting an oil-soluble phenolic or alcoholic material, such as alkylphenol, with an aldehyde, such as formaldehyde or acetaldehyde, and a nitrogen-containing compound. Typical Mannich bases contain from about 8 to 28 or more carbon atoms in the alkyl group. If desired, the alkaline earth metal salt of the phenolic-type Mannich base may be used as a suspending agent.

REACTION PROMOTER

When conducted in a hydrocarbon medium, a reaction promoting amount of a hydroxylic promoter is necessary for the reaction to proceed at an acceptable rate. Generally from 0.1 to 10 weight percent or more of the reaction mixture may be the hydroxylic promoter. The promoter is believed to function as a solubilizing agent for the basically reacting metal compound. The promoter is preferably water or an alkanol of 1 to 6 carbon atoms or an alkanediol of 2 to 6 carbon atoms such as methanol, ethanol, isopropanol, butanol, ethylene glycol, 1,4-butanediol and the like. Most preferred are water, ethanol, and methanol. Mixtures of these promoters may be used as desired to keep water formed in the reaction in solution.

CARBON DIOXIDE

Preferably gaseous carbon dioxide is bubbled through the reaction mixture to form the carbamate. It can also be added in the liquid or solid state.

SOLVENT

The reaction is carried out in a suitable solvent. Preferably the solvent is a lubricating oil so that no removal of the solvent is necessary before incorporation of the additive into the lubricating oil. Other useful solvents are lower-boiling hydrocarbon solvents such as hexane or hydrocarbon thinner. Mixtures of lubricating oil with hexane or hydrocarbon thinner are also useful. After preparation is complete, the lower-boiling solvents are readily removed by heating, if desired.

The reaction may also be carried out in water. The resulting solution of the N-carboxyamino acid magnesium salt may be dispersed with the aid of a dispersing agent, in the desired hydrocarbon solution and the water subsequently removed by dehydration to form a dispersion of the salt or the resulting water solution may be evaporated to dryness, the resulting solid ground to a finely-divided state, and dispersed with the aid of dispersing agents in the desired hydrocarbon medium.

REACTION CONDITIONS

The process of this invention may be carried out at any temperature from the freezing point of the mixture to its boiling point. Ordinarily the reaction is conducted at a temperature of from 0° to 75° C., preferably 20° to 75° C. and most preferably 25° to 50° C. While the reaction proceeds satisfactorily at atmospheric pressure, higher or lower pressures may be used if desired.

The ratio of the suspending agent to the carbon dioxide and the amino acid is such that from about $\frac{1}{3}$ to $\frac{3}{4}$ of the alkalinity value of the final composition is contributed by the ashless amino-containing material. Preferably it is desirable to have about one equivalent of the amino compound for each equivalent of the basically reacting magnesium compound. Under typical conditions and based on 1 equivalent of the basically reacting magnesium compound, the reaction mixture would contain from 0.3 to 2.0, preferably from 0.5 to 1.5, equivalents of the amino compound; from 1 to 3, preferably 1.5 to 2.5, equivalents of carbon dioxide; and from 2 to 20, preferably 4 to 10, parts by weight of the suspending agent per part of the basically reacting magnesium compound. The hydrocarbon solvent should be present in sufficient amount to enable good mixing of the reactants and is usually present as from 5 to 50 and preferably 10 to 25 milliliters per gram of basically reacting magnesium compound. From 0 to 5, preferably 1 to 2, milliliters of the promoter per gram of basically reacting magnesium compound is also used.

In a preferred method for carrying out the reaction, a sodium, calcium or magnesium alkylbenzene sulfonate is used as the suspending agent. It is also preferred to use an alkenylsuccinimide or an alkenylsuccinic anhydride as a co-suspending agent.

LUBRICANT COMPOSITIONS

When used as a lubricating oil additive, the compositions prepared by this invention provide a high alkalinity value at a lower ash content than is present in most conventional dispersants and/or acid-neutralizers used as lubricating oil additives.

Alkalinity value is one method of specifying the degree of overbasing of the lubricating oil composition. It is also a measure of the acid-neutralizing properties of the composition. The method for determining the alkalinity value commonly used for a composition is set forth in ASTM Method D-2896. Briefly, the alkalinity value is the total base number given as milligrams of potassium hydroxide per gram of sample. It is the quantity of potassium hydroxide required to neutralize the same amount of perchloric acid that 1 gram of the sample neutralizes. For example, if a composition has the same acid-neutralizing capacity per gram as 10 mg of potassium hydroxide, the composition is given an alkalinity value of 10. The lower limit of alkalinity value is 0 for a neutral composition. Values of 200 or more are especially desirable for use in lubricants which are exposed to the decomposition products of sulfur-containing diesel fuels. Typical alkalinity values for additive compositions of this invention range from about 30 to 400 or more.

Lubricant compositions containing the additives of this invention are prepared by admixing through conventional admixing techniques the appropriate amount of the additive of this invention with a lubricating oil. The selection of a particular base oil depends on the contemplated application of the lubricant and on the presence of other additives. Generally, the amount of additive of this invention used in the lubricating oil will vary from 0.1 to 40% weight, and preferably from 2 to 35% by weight. The resulting lubricating oil will usually have an alkalinity value in the range of 1 to 120, preferably 2.5 to 100.

The lubricating oil which may be used in this invention includes a wide variety of hydrocarbon oils such as naphthenic bases, paraffin bases and mixed-base oils. The lubricating oils may be used individually or in combination and generally have a viscosity which ranges from 50 to 5000 SUS (Saybolt Universal Seconds) and usually from 100 to 1500 SUS at 38° C.

In many instances it may be advantageous to form concentrates of the additives of this invention within a carrier liquid. These concentrates provide a convenient method of handling and transporting the additives of this invention before their subsequent dilution and use. The concentration of the additives of this invention within the concentrates may vary from 85 to 10% by weight, although it is preferred to maintain the concentration between about 15 and 40% by weight. The preferred method of obtaining concentrates is to carry out the preparation of the additive in a limited amount of lubricating oil, as will be used in making the final dilute lubricant composition. Alternatively, the additive may be prepared in a low-boiling hydrocarbon which is removed by distillation after adding a limited amount of lubricating oil.

As desired, other additives may be included in the lubricating oil compositions of this invention. These additives include antioxidants or oxidation inhibitors, dispersants, rust inhibitors, anticorrosive agents, and so forth. Other types of lubricating oil additives which may be employed include antifoam agents, stabilizers, antistain agents, tackiness agents, antichatter agents, dropping point improvers, antisquawk agents, extreme-pressure agents, odor control agents, and the like.

EXAMPLES

The following examples are presented to illustrate this invention, and are not in any way to be interpreted as limiting the scope of the invention.

EXAMPLE 1

To a 2-liter, 3-neck flask was added 37.5 g (0.5 mole) glycine and 1000 ml water. The resulting solution was chilled to 15° and sparged with a total of 283 g (6.4 mole) carbon dioxide over a 3-hour period. During this time a total of 20.9 g (0.52 mole) magnesium oxide was added in several portions to the mixture. The resulting clear solution was allowed to stand at room temperature overnight, then filtered to obtain 1063 g of filtrate which had an alkalinity value of 70.9 (87% yield). A portion (41.9 g) of the filtrate was evaporated to dryness to yield 2.84 g white solids which had an alkalinity value of 1001.4 and contained 12.7% Mg, 8.58% N, 20.51% C, and 4.36% H. Calculated for $C_3H_3NO_4Mg \cdot 2H_2O$% C 20.3; %H 3.95; %N 7.90; %Mg 13.7; Alkalinity value 949.

EXAMPLE 2

To a 250 ml Erlenmeyer flask was added 7.9 g (0.1 mole) ammonium bicarbonate, 2.01 g (0.05 mole) magnesium oxide, 100 ml distilled water, 4.9 g (0.1 mole) sodium cyanide. The mixture was stirred and 8.1 g (0.1) mole of a 37% solution of formaldehyde was added dropwise over 2 minutes. The mixture was stirred and let stand overnight. Then an additional 50 ml of water was added and 2.0 g magnesium oxide while carbon dioxide was bubbled through the mixture. A total of 11.5 g of carbon dioxide was added. The mixture was filtered and the filtrate evaporated to near dryness on a hot plate. A crude product of magnesium glycine carbamate was obtained (11.52 g) having an alkalinity value of 694 and containing 6.2% magnesium, 855 ppm calcium, 1.7% sodium and 9.8% nitrogen.

EXAMPLE 3

Into each of three 50 ml beakers was placed 20 ml of distilled water. Into beaker #1 was placed 50 mg. magnesium oxide and 60 mg. glycine. Into beaker #2 was placed 50 mg magnesium oxide. Into beaker #3 was placed 50 mg magnesium oxide and 60 mg glycine. The mixtures in all beakers were stirred. Carbon dioxide was added to beaker #1 and the solution was nearly clear after 0.5 hour. No carbon dioxide was added to beaker #2 and the solids were still suspended after 1 hour. Then carbon dioxide was added to beaker #2 for 0.5 hour with no apparent change in the suspended solids. There was no change in beaker #3 after 0.5 hour of stirring and then carbon dioxide was added and all of the magnesium oxide dissolved after 0.5 hour to give a clear solution.

From the above it was concluded that the reaction of magnesium oxide was greatly promoted by the glycine. Also, the magnesium glycine carbamate reaction product was refluxed on a hot plate and surprisingly did not form a precipitate.

EXAMPLE 4

To a 1-liter, 3-neck flask was charged 180 grams of a 67% concentrate of a calcium alkylated aromatic sulfonate hydrocarbon thinner. 400 ml of a hydrocarbon thinner, 10.3 grams (0.25 mol) magnesium oxide (Maglite A, Merck, 200 m²/gm), 18.8 grams (0.25 mol) glycine and 10.0 mls water. The mixture was stirred at room temperature and warmed to 40° C. and then 3 grams of carbon dioxide was added over a 25 minute period at a temperature of from 40° to 45° C. Then 10 mls of 100% ethanol was added and 2 grams of carbon dioxide was added over a period of 20 minutes at temperatures ranging from 45° to 55° C. An additional 5 mls of 100% ethanol was added and an additional 8 grams of carbon dioxide was added over a period of 76 minutes at 55° C. The reaction mixture was then centrifuged for 20 minutes at 12,000 RPM and then filtered through a pad of diatomaceous earth. The filtrate was stripped at 110° C. at 20 mm Hg pressure. The mixture yielded 142 grams of product having an alkalinity value of 189.8, and containing 3.22% magnesium, 1.33% calcium, and 1.24% nitrogen.

EXAMPLE 5

To a 5-liter, 3-neck flask was charged 670 grams of a 67% concentrate of a calcium alkylated aromatic sulfonate in hydrocarbon thinner, 2330 grams of a hydrocarbon thinner, 47 mls water, 75 mls 95% ethanol, 50.5 grams magnesium oxide, 94.0 grams glycine. The mixture was stirred and heated to 40° C. 56 grams of carbon dioxide was added over 2 hours 15 minutes while the temperature ranged from 38° to 47° C. The reaction mixture was filtered through a pad of diatomaceous earth. The filtrate was stripped at 110° C. at 20 mm Hg pressure. The mixture yielded 826 grams of product having an alkalinity value of 203.6 and containing 3.08% magnesium, 1.38% calcium, and 1.39% nitrogen.

EXAMPLE 6

To a 1-liter, 3-neck flask was charged 150 grams of a calcium alkylated aromatic sulfonate 450 mls of a hydrocarbon thinner, 20 mls of methanol, 10 mls of water, 37.5 grams glycine (0.5 mole), and 20.6 grams magnesium oxide. The mixture was stirred and heated to 45° C. and 25 grams of carbon dioxide was added over 5 hours and 13 minutes while the temperature ranged from 33° C. to 48° C. The reaction mixture was filtered through a pad of diatomaceous earth. The filtrate was stripped at 110° C. at 20 mm Hg pressure. The mixture yielded 184 grams of product having an alkalinity value of 282.4 and containing 4.94% magnesium, 1.27% calcium, and 1.8% nitrogen.

EXAMPLE 7

To a 5-liter, 3-neck flask was charged 900 grams of a calcium alkylated aromatic sulfonate, 2,300 mls of a hydrocarbon thinner, 120 mls of methanol, 120 mls of water, 210 grams (2.8 mols) glycine and 153.2 grams (3.8 mols) magnesium oxide. The mixture was stirred for 5 minutes at room temperature and then 126 grams of carbon dioxide and 30 mls of water were added over 8 hours with the temperature ranging from 28° to 41° C. The reaction mixture was filtered through a pad of diatomaceous earth. The filtrate was stripped to 115° C. at 20 mm Hg pressure. The mixture yielded 1188 grams of product having an alkalinity value of 332.6, and containing 5.98% magnesium, 1.04% calcium, and 2.05% nitrogen.

What is claimed is:

1. A magnesium salt of an N-carboxyamino acid.
2. A compound of claim 1 wherein said salt is the magnesium salt of an alpha amino acid.
3. A compound of claim 1 wherein said amino acid is selected from glycine, alpha- or beta-alanine, cysteine, methionine, sarcosine or lysine.
4. A compound of claim 3 wherein said salt is the magnesium salt of N-carboxyglycine.
5. A lubricating oil composition comprising an oil of lubricating viscosity and from 0.5 to 30% by weight of the composition of claim 1, 2, 3 or 4.
6. A lubricating oil concentrate which comprises from 10 to 80% by weight of an oil of lubricating viscosity and from 90 to 20% by weight of the composition of claim 1, 2, 3 or 4.

* * * * *